US006150400A

United States Patent [19]
Nyirjesy et al.

[11] Patent Number: 6,150,400
[45] Date of Patent: Nov. 21, 2000

[54] METHOD FOR TREATING VULVAR VESTIBULITIS

[75] Inventors: Paul Nyirjesy, Rydal; Steven P. Gelone, Wyndmoor, both of Pa.

[73] Assignee: Presutti Laboratories, Arlington Heights, Ill.

[21] Appl. No.: 09/219,975

[22] Filed: Dec. 23, 1998

Related U.S. Application Data

[63] Continuation-in-part of application No. PCT/US98/13193, Dec. 9, 1998.
[60] Provisional application No. 60/051,264, Jun. 30, 1997.

[51] Int. Cl.$^7$ .................................................. A61K 31/35
[52] U.S. Cl. ................................................................ 514/456
[58] Field of Search .............................................. 514/456

[56] References Cited

U.S. PATENT DOCUMENTS

| | | | |
|---|---|---|---|
| 3,419,578 | 12/1968 | Fitzmaurice et al. | 167/54 |
| 3,686,412 | 8/1972 | Fitzmaurice et al. | 424/283 |
| 4,192,860 | 3/1980 | Griffiths | 424/43 |
| 4,271,182 | 6/1981 | Sullivan | 424/283 |
| 4,362,742 | 12/1982 | Sullivan | 424/283 |
| 5,532,270 | 7/1996 | Clemente et al. | 514/456 |
| 5,576,346 | 11/1996 | Clemente et al. | 514/456 |

OTHER PUBLICATIONS

Facts and Comparisons, Olin et al., St. Louis, Mo: J B Lippincott, pp. 182g–h, 183 and 825, Jul. 1987.
Ariyanayagam, Mrin, et al., *British Journal of Dermatology*.112:343–348, (1985).
Bosso, John V., M.D., *Allergy Proc.* 12:2,113–116, (1991).
Chaim, Walter, et al., *European Journal of Obstetrics & Gynecology and Reproductive Biology* 68:165–168, (1996).
Dworetzky, Murray M.D. and Galland, Leo M.D., *Am J. Obstet Gynecol.*, Correspondence 161:6,1752–1753 (1989).
Fidel, Paul L., et al., *Clinical Microbiology Review*, 9:(3) 335–348 (1996).
Fitzpatrick, Christopher C., et al., *Obstetrics & Gynecology*, 81:(5)Part 2 860–862 (1993).
Fredrich Edward, G., *The Journal of Reproductive Medicine*, 32:(2)111–114, (1987).
Herod, J.J.O. et al., *British Journal of Obstetrics and Gyneacology*, 103:446–452, (1996).
Kalo–Klein, Aliza et al., *Am J. Obstet Gynecol*, 161:(5), 1132–1136, (1989).
Kalo–Klein, Aliza et al., *Am J. Obstet Gynecol*, 164:(5) Part 1, 1351–1354, (1991).
Kudelko, N.M. M.D., *Annals Of Allergy*, 29:266–267, (1971).
Marinoff, Stanley, C., et al., *Am J. Obstet Gynecol*, 163:(4) Part 2, 1228–1233, (1991).
Nyirjesy, Paul et al., *Infectious Diseases in Obstetrics and Gynecology*, 3:193–197. (1995).
Paavonen, Jorma, *Acta Obstet Gynecol Scand.* 74:243–247, (1995).
Pyka, Ronald, E., et al., *International Journal of Gynecological Pathology*, 7:249–257, (1988).
Saban, Ricardo, et al., *Seminars in Urology*, IX:2, 88–101, (1991).
Witkins, Steven S., PhD., *Clinical Obstetrics and Gynecology*, 34:3, 662–667, (1991).
Witkins, Steven S., et al., *J. Allergy Clin. Immunol*, 81:2, 412–416, (1988).
Witkins, Steven S., et al., *The Journal of Infectious Diseases*, 164:396–399, (1991).
Witkins, Steven S., *American Journal of Reproductive Immunology and Microbiology*, 15:34–37, (1987).

*Primary Examiner*—Minna Moezie
*Assistant Examiner*—Shengjun Wang
*Attorney, Agent, or Firm*—Rockey, Milnamow & Katz, Ltd.

[57] ABSTRACT

The present invention provides an improved method for treating vulvar vestibulitis in a patient, comprising applying to the vestibule or the vestibule and the vagina of a patient an effective amount of a composition comprising a compound which inhibits the release of mediators from mast cells. The method is simple, inexpensive, well tolerated, and effective in the majority of cases.

17 Claims, No Drawings

METHOD FOR TREATING VULVAR VESTIBULITIS

CROSS-REFERENCE TO RELATED APPLICATIONS

This patent application is a continuation-in-part of a co-pending U.S. patent application filed on Dec. 9, 1998 under Sec. 371 from PCT/US98/13193, having an international filing date of Jun. 25, 1998; which invention claims the benefit of U.S. provisional application Ser. No. 60/051,264, filed Jun. 30, 1997.

FIELD OF THE INVENTION

This invention relates to methods and compositions for the treatment of vulvar vestibulitis.

BACKGROUND OF THE INVENTION

A) Vulvar Vestibulitis

Vulvar vestibulitis syndrome (herein "vulvar vestibulitis") is a subtype of vulvodynia.

Vulvodynia is a complex gynecologic syndrome characterized by unexplained vulvar pain, sexual dysfunction, and psychological disability. It is one of the most perplexing problems faced by the practicing gynecologist. Although the exact prevalence of vulvodynia is unknown, the condition is relatively common. In a vaginitis referral population symptoms are present in as many as 15–20% of the patients seen. It has been estimated that 1½ million American women may suffer from some degree of vulvodynia. Vulvodynia can have multiple etiologies, and several subtypes have been recognized.

The most common subtype of vulvodynia is vulvar vestibulitis, which has been called "focal vulvitis" and "vestibular adenitis." Vulvar vestibulitis presents a constellation of symptoms involving and limited to the vulvar vestibule. The criteria for recognizing vulvar vestibulitis include: (1) pain on vestibular touch or attempted vaginal entry, (2) tenderness to Q-tip pressure localized within the vulvar vestibule, (3) physical findings confined to vestibular erythema of various degrees, and (4) an exclusion of other causes for vestibular erythema and tenderness, such as candidiasis (yeast infections) or herpes infections. Other symptoms include itching, swelling and excoriation.

The pain in vulvar vestibulitis may be described as sharp, burning, or a sensation of rawness. In severe cases, dyspareunia totally prohibits sexual intercourse. Pain may also be elicited on tampon insertion, biking, or wearing tight pants. The erythema may be diffuse or focal, and may be localized around the orifices of the vestibular glands or at the fourchette. In addition, patient symptoms may often include itching. Morbidities extend well beyond the local symptoms, with many women undergoing tremendous changes in psychosexual self-image, and can include profound adverse effects on marriages and other important relationships.

Vulvar vestibulitis may be acute or chronic. In one study, an arbitrary cutoff of three months of symptoms was used to distinguish between the acute and chronic forms (Marinoff and Turner, *Am. J. Obstet. Gynecol.* 165:1228–33, 1991). Most clinicians use an arbitrary cutoff of six months to distinguish between the acute and chronic forms. Several investigators have attempted to find a common histopathological aspect to vulvar vestibulitis, but have failed to do so.

Pyka et al. studied the histopathology of vulvar vestibulitis in specimens from 41 patients who had vulvar surgery for treatment of the syndrome (*Int. J. Gynecol. Pathol.* 7:249–57, 1988). They reported a mild to moderate mixed chronic inflammatory response. The infiltrate was characterized by lymphocytes and plasma cells, with only small numbers of polymorphonuclear leukocytes. Minor vestibular glands showed varying degrees of squamous metaplasia and were not affected by inflammatory cells. No fungi, gram-positive bacteria, mycobacteria, spirochetes, or Donovan bodies were detected. There was no evidence of an allergic phenomenon or an immediate hypersensitivity reaction, each of which would have exhibited characteristics histologic findings.

The causes of vulvar vestibulitis are multifactorial. Known and suspected causes of the acute form include fungal or bacterial infection (e.g. Candida, Trichomonas), chemical irritants (e.g. soaps, douches, sprays), therapeutic agents (e.g. antiseptics, suppositories, creams, 5-fluorouracil methods (e.g. cryosurgery, laser treatment), and allergic drug reactions. In the acute form, treatment of the presumed cause may lead to rapid relief.

Vulvar vestibulitis may become chronic if the cause becomes persistent or recurrent. Chronic vulvar vestibulitis may also persist long after all suspected causes have been treated. And many causes of chronic vulvar vestibulitis are of unknown etiology. Although no direct cause and effect relationship has been shown, it has been suggested that oxalates in the urine, altered vaginal pH, localized peripheral neuropathy, and subclinical viral infections can all contribute to the syndrome. A history of fungal infection is present in most patients who have vulvar vestibulitis, suggesting that recurrent yeast infections may somehow play a role in the initiation of the syndrome. It has been suggested that conditions such as recurrent candidiasis may lead to local changes in the vaginal immune system, including both Th1 and Th2 type responses (Fidel and Sobel, *Clin. Microbiol. Reviews* 9(3):335–48, 1996).

Because of its multiple causes, and its frequently unknown causes, vulvar vestibulitis can be very difficult to treat. Patients frequently suffer through a period of misdiagnosis, and may present with a long history of unsuccessful attempts at therapy.

B) Treatment of Vulvar Vestibulitis

The first-line therapy for vulvar vestibulitis is the treatment of its suspected causes. This includes the pharmacologic treatment of infections and the discontinued use of the irritants and therapeutic agents, local and systemic, that may contribute to the problem. Topical anesthetics, corticosteroids, and sex hormones may provide some symptomatic relief.

In many cases, treatment of the suspected causes does not lead to a cure. Further treatments may include dietary modifications, physical therapy and biofeedback, use of topical, oral, or injected therapeutic agents, or surgery. Unfortunately, no single treatment works in all patients. Moreover, many of these approaches involve complex medical procedures, significant costs, and/or undesirable side effects.

In the dietary approach, a low oxalate diet is combined with calcium citrate supplementation. One disadvantage to this approach is that it can be difficult to consistently modify eating habits. Another disadvantage is that the foods which must be avoided include those that are generally though to be important in a healthy diet (e.g. cruciferous vegetables).

Physical therapy and biofeedback, to strengthen the pelvic muscles and break the cycle of muscle spasm, may provide relief in some patients. This approach is very labor intensive and expensive, and does not always provide relief.

Topical therapeutic agents which have been used in the treatment of vulvar vestibulitis include corticosteroids, estrogen, progesterone, and capsaicin cream.

Oral therapeutic agents which have been used in the treatment of vulvar vestibulitis include isotretinoin, dapsone, acyclovir, and tricyclic anti-depressants such as amitriptyline. In addition to having variable therapeutic effects, each of these agents can cause undesirable side effects. Isotretinoin can cause mucocutaneous, gastrointestinal, cerebral, ocular and metabolic side effects, as well as severe fetal malformation in the event of pregnancy. Dapsone can cause anemia, jaundice, gastrointestinal distress, and weakness, and requires the monitoring of hemoglobin, hematocrit, and white cell count. Acyclovir can cause headaches and mild gastrointestinal upset. And the side effects of the tricyclic antidepressants include drowsiness, weight gain, and dry mouth.

Intralesional alpha-interferon injections may provide relief from vulvar vestibulitis in some patients.

Nyirjesy and Halpern have described a sequential treatment study, designed to assess the efficiency of medical (rather than surgical) management of vulvar vestibulitis, and to determine whether historical variables could be used to predict which treatments would be successful (*Infectious Diseases in Obstetrics and Gynecology* 3:193–97, 1995). Seventy-four patients were treated using a sequence of consecutive medical therapies: topical aqueous 4% lidocaine with intercourse, topical corticosteroid therapy, oral amitriptyline, topical low-dose 5-fluorouracil (5-FU) cream, intralesional alpha-interferon, and a low-oxalate diet in combination with oral calcium citrate. The patients were followed over 3–30 months. Forty-nine patients (66.2%) reported positive responses, including 18.1% of the patients who used lidocaine, 33.8% who used topical corticosteroids, 57.1% who used amitriptyline, 16.7% who used 5-FU, none who received interferon, and 50% who tried a low-oxalate diet. No historical variables were predictive of which therapies would have the most successful outcome.

Surgery is the treatment of choice for severe incapacitating cases of vulvar vestibulitis that do not respond to the more conservative treatments described above. Perineoplasty, also called vestibulectomy, is carried out under general anesthesia. An outer incision line is made from the periurethral glands on one side, along Hart's line, down into and including a good portion of the fourchette and back along Hart's line to the periurethral glands on the other side. An inner incision line is made behind the hymenal ring. The horseshoe-shaped tissue between these lines is excised, and the vagina is mobilized and advanced onto the perineum to cover the defect. Care must be taken to identify the bladder and rectum. Complications of surgery can include wound hematoma, dehiscence, uneven healing, and duct stenosis with cyst formation. At least 5–10% of patients are not cured even with surgery.

Superficial laser ablation of the vestibule has been used as an alternative to surgery, but in general the results have been disappointing. The procedure requires a prolonged healing time, and after treatment the symptoms are frequently the same or worse than before treatment.

There is a need for improved methods for treating vulvar vestibulitis, especially those cases of unknown etiology and those cases that fail to respond to the treatment of suspected causes.

C) Mast Cells

Mast cells, which are derived from bone marrow progenitors, play a role in immediate hypersensitivity and other inflammatory reactions by releasing a variety of chemical mediators upon activation. These mediators, some of which are stored as granules in the cytoplasm, include biogenic amines such as histamine, lipid mediators such as leukotrienes, prostaglandins, and platelet-activating factor, cytokines, and enzymes. Mast cells can be activated by crosslinking of surface IgE attached to FCεRI, by chemokines, cytokines, neurotransmitters and other activating agents, or by local trauma.

Saban et al. reported high densities of mast cells in bladder biopsies from interstitial cystitis (an idiopathic inflammatory syndrome of the urogenital tract) subjects (*Semin. Urol.* IX:88–101, 1991). It has been speculated that the tissues involved in interstitial cystitis and vulvar vestibulitis may share a common embryologic origin and therefore be predisposed to similar pathological response (Fitzpatrick et al., *Obstet. Gynecol.* 81:860–62, 1993). Histopathological studies of specimens from vulvar vestibulitis subjects, however, report the presence of varying numbers of mast cells. Using a special toluidine blue staining, Pyka et al. found mast cells in only three of fourteen (21 %) cases of vulvar vestibulitis (*Int. J. Gynecol. Pathol.* 7:249–57, 1988). Chaim et al., in contrast, used a special Giemsa stain and identified large numbers of mast cells in sixteen of sixteen vulvar vestibulitis subjects undergoing surgical intervention (*Eur. J. Obstetrics & Gynecol. And Reproductive Biol.* 68:165–68, 1996). Chaim et al. speculated that pathways of mast cell activation at the bladder level may also be involved in the etiology of pure idiopathic vulvar vestibulitis. Chaim et al. also found mast cells in vulvar tissues of patients with vulvar displasia and suggested that mast cells may not be specific for vulvar vestibulitis syndrome.

D) Compounds Which Inhibit the Release of Mediators from Mast Cells

Immediate hypersensitivity reactions, including the release of mediators from mast cells, cause various allergic diseases in susceptible individuals. Compounds which inhibit the release of mediators from mast cells are said to "stabilize" mast cells, and are used for the treatment of human allergy. Various compounds, including cromolyn compounds, nedocromil compounds, and others, are known to inhibit the release of mediators from mast cells.

Cromolyn or cromoglycic acid ($C_{23}H_{16}O_{11}$, 1,3-bis(2-carboxychromon-5-yloxy)-2-hydroxypropane), a chromone complex that inhibits the release of mediators from mast cells and blocks mast cell degranulation, has the following structure (I):

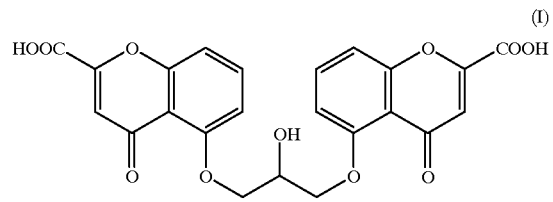

(I)

The disodium salt of cromolyn ($C_{23}H_{14}Na_2O_{11}$, cromolyn sodium, disodium cromoglycate, sodium cromoglycate) is a water soluble, odorless, white, hydrated crystalline powder.

Cromolyn sodium, which inhibits the release of histamine and other mediators from mast cells that have been sensitized by specific antigens, is used pharmacologically as an antiasthmatic/antiallergic. Oral formulations of cromolyn sodium are used to treat the diarrhea, flushing, headaches, vomiting, urticaria, abdominal pain, nausea, and itching of mastocytosis, which is an accumulation of mast cells in the tissues. Opthalmic and nasal solutions of cromolyn sodium are used to treat the itching, redness, swelling, sneezing, tearing, and discharge of allergic conjunctivitis and allergic rhinitis. And inhalation aerosols of cromolyn sodium are used as prophylactic agents in the management of asthma.

Cromolyn sodium has been used to manage the symptoms of allergic vaginitis generally and seminal fluid hypersensitivity specifically. It has also been used in patients with vulvar intraepithelial neoplasia.

Allergic vaginitis includes IgE-mediated reactions to antigens in seminal fluid and to atmospheric allergens such as pollen. Allergic vaginitis is characterized by vaginal itching and burning pain or discomfort on coitus. It has been reported that cromolyn sodium solutions, used as a vaginal douche or injected intravaginally using a rubber ear syringe, can provide some relief from the symptoms of allergic vaginitis (Dworetzky and Galland, *Am. J. Obstet. Gynecol.* 161(6):1752–53, 1989).

Seminal fluid hypersensitivity is an allergic reaction to antigens in the seminal component of male ejaculate. Seminal fluid hypersensitivity is characterized by a spectrum of local and systemic hypersensitivity reactions, which can include postcoital vulvovaginal itching, swelling, redness, fixed cutaneous eruptions, burning, and pain, with or without the progression to systemic anaphylaxis. These hypersensitivity reactions can be prevented by avoiding contact with seminal fluid, through abstinence or the use of condoms. It has been reported that a 4% cromolyn sodium cream, applied intravaginally, can prevent local and cutaneous hypersensitivity reactions to seminal fluid (Bosso et al., *Allergy Proc.* 12(2):113–16, 1991).

Herod et al. briefly mentioned the use of sodium cromoglycate in patients with vulvar intraepithelial neoplasia, a pre-invasive form of vulvar cancer, but did not disclose what formulation of sodium cromoglycate was used, whether the treatment was oral or topical, or the specific results obtained (*Br. J. Obstet. Gynaecol.* 103:446–52, 1996).

Nedocromil ($C_{19}H_{17}NO_7$, 9-ethyl-6,9-dihydro-4,6-dioxo-10-propyl-4H-pyrano[3,2-g]quinoline-2,8-dicarboxylic acid) is another compound known to inhibit the release of mediators from mast cells. Nedocromil has the following structure (II):

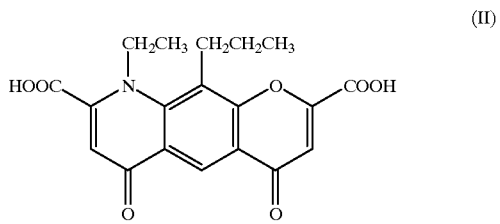

(II)

The disodium salt of nedocromil ($C_{19}H_{17}NNa_2O_7$, nedocromil sodium) is a water soluble pale yellow powder, which is used as an inhalation therapy for the management of bronchial asthma.

SUMMARY OF THE INVENTION

The present invention relates to the discovery of an effective method of treating vulvar vestibulitis. Although most cases of vulvar vestibulitis have no known or suspected allergy-based etiology, the present invention discloses that compositions comprising cromolyn sodium are generally useful in the treatment of this syndrome. Without wishing to be bound to a theory, the inventors hypothesize that many cases of vulvar vestibulitis represent a condition which is the result of recurrent candidiasis, where the yeast infections themselves may be treated but local increase in inflammatory cells, particularly mast cells, leads to persistent pain in the area. By inhibiting the release of mediators from mast cells, symptoms of vulvar vestibulitis are alleviated. The invention provides a simple and well tolerated method of treatment, which is effective in most cases.

The invention provides a method of treating vulvar vestibulitis in a patient which comprises applying to the vestibule or to the vestibule and the vagina of the patient an effective amount of a composition comprising a compound which inhibits the release of mediators from mast cells.

In a preferred embodiment, the composition comprises cromolyn or a salt thereof. In a more preferred embodiment the composition comprises cromolyn sodium. The composition preferably comprises from about 1% to about 10%, more preferably from about 2% to about 6%, and most preferably about 4%, by weight of cromolyn sodium.

In another preferred embodiment, the composition comprises nedocromil or a salt thereof. In a more preferred embodiment the composition comprises nedocromil sodium. The composition preferably comprises from about 1% to about 10%, more preferably from about 2% to about 6%, and most preferably about 4%, by weight of nedocromil sodium.

In some embodiments, the composition comprises a cream base. In other embodiments, the composition comprises an ointment base or a gel base.

The composition may also contain additional ingredients such as an antiseptic, a preservative, a detergent, a buffer, or an anesthetic.

The composition is preferably applied to the vestibule from about one to about three times per day, or to the vestibule and the vagina from about one to about two times per day.

The invention also constitutes the use of a compound which inhibits the release of mediators from mast cells for the preparation of a medicament for the treatment of vulvar vestibulitis.

The invention further provides a pharmaceutical composition comprising a compound which inhibits the release of mediators from mast cells for the treatment of vulvar vestibulitis. In a preferred embodiment the composition comprises nedocromil sodium in a cream, gel or ointment base. The composition preferably comprises from about 1% to about 10%, more preferably from about 2% to about 6%, and most preferably about 4%, by weight of nedocromil sodium.

Other aspects and advantages of the present invention are described in the following detailed description of the preferred embodiments thereof.

DETAILED DESCRIPTION OF THE INVENTION

The inventors have discovered an improved method for treating vulvar vestibulitis, which comprises the topical application of a composition comprising a compound which inhibits the release of mediators from mast cells. This method is simple, inexpensive, well tolerated and effective in the majority of cases. The method provides effective relief without the need for surgery and without the side effects associated with many other treatment modalities.

A) Definitions

The following definitions are used throughout the specification, and are intended as an aid to understanding the scope and practice of the present invention.

"Cromolyn" is cromoglycic acid.

"Cromolyn sodium" is the disodium salt of cromoglycic acid.

"Dyspareunia" means painful coitus.

"Erythema" means redness of the skin.

"Nedocromil Sodium" is the disodium salt of nedocromil.

"Vulva" means the external genitalia of the female, including the mons pubis, the labia majora and minora, the clitoris, and the vestibule.

"Vulvar" means relating to the vulva.

"Vestibule" or "vulvar vestibule" is the space behind the glands clitoridis and between the labia minora, containing the openings of the vagina and urethra, and ducts of the vestibular glands.

"Vestibular" means relating to the vestibule.

"Vulvodynia" is chronic unexplained vulvar discomfort, characterized by complaints of burning and sometimes stinging, irritation, or rawness.

"Vulvar vestibulitis" or "vulvar vestibulitis syndrome" is a subtype of vulvodynia characterized by one or more of the following symptoms: inflammation of the vulvar vestibule and the periglandular and subepithelial stroma, complaints of burning and dyspareunia, rawness, irritation, itching and swelling.

B) Formulation of Compositions According to the Invention

The present invention is directed to methods of treating vulvar vestibulitis comprising applying to the vestibule or to the vestibule and the vagina, an effective amount of a composition comprising a compound which inhibits the release of mediators from mast cells.

In a preferred embodiment the compound is cromolyn or nedocromil or a salt of cromolyn or nedocromil. In a most preferred embodiment, the composition comprises about 4% by weight of cromolyn sodium in a hydrophilic cream base. Other compounds that inhibit the release of mediators from mast cells can also be used according to the invention.

Examples of other compounds that inhibit the release of mediators from mast cells include olopatadine ((Z)-11-(3-(dimethylamino)propylidene)-6,11-dihydrodibenz(b,e) oxepine-2-acetic acid hydrochloride), amlexanox ($C_{16}H_{14}N_2O_4$; 2-Amino-7-(1-methylethyl)-5-oxo-5H-[1] benzopyrano(2,3-b)pyridine-3-carboxylic acid), ketotifen ($C_{19}H_{19}NOS$; 4,9-Dihydro-4-(1-methyl-4-piperidinylidene)-10H-benzo[4,5]cyclohepta[1,2-b]thiophen-10-one) and ketotifen fumarate ($C_{23}H_{23}NO_5S$), lodoxamide tromethamine (N,N'-(2-chloro-5-cyano-m-phenylene) dioxamic acid tromethamine salt), minocromil (6-Methylamino-4-oxo-10-propyl-4H-pyrano[3,2-g] quinoline-2,8-dicarboxylic acid) and its sodium salt, repirinast ($C_{20}H_{21}NO_5$; 5,6-Dihydro-7,8-dimethyl-4,5-dioxo-4H-pyrano[3,2-c]quinoline-2-carboxylic acid 3-methyl-butylester), suplatast tosylate ((+/−)-(2-{[p-(3-Ethoxy-2-hydroxypropoxy)phenyl]carbamoyl}ethyl]dimethyl sulphonium p-toluenesulphonate), tiacrilast ((E)-6-(methylthio)-4-oxo-3(4H)-quinazolineacrylic acid) and its sodium salt, tranilast ($C_{18}H_{17}NO_5$; 2[[3-(3,4-Dimethoxyphenyl)-1-oxo-2-propenyl]amino]benzoic acid), taxanox ($C_{13}H_6ClN_5O_2$; 9-Chloro-7-(1H-tetrazol-5-yl)-5H-[1]benzopyrano[2,3-b]pyridin-5-one) and its sodium salt, and zaprinast (1,4-Dihydro-5-(2-propoxyphenyl)-1,2,3-triazolo[4,5-d]pyrimidin-7-one.

Salts that may be used according to the invention include ammonium salts, alkali metal (such as sodium, potassium, or lithium) salts, alkaline earth metal (such as magnesium or calcium) salts, and salts with organic basis (such as amine salts like piperidine, triethorolamine, or diethylaminoethyl amine salts).

The compound which inhibits the release of mediators from mast cells may be formulated into any composition which is suitable for topical application. These compositions include solutions, gels, pastes, ointments, and creams. The preferred composition is an ointment or cream; the most preferred composition is a cream.

Ointments are preparations in which the drug is suspended or dissolved in a grease or oil. Petrolatum, liquid petrolatum (mineral oil), olive oil, lanolin, or other animal fats may be used. Ointments provide mechanical protection to the underlying skin and are able to penetrate thickened lesions to deliver the contained medication. They lubricate and soften the skin but do not permit drainage or evaporation from the skin.

Creams, which are sometimes called water-containing ointments or hydrophilic ointments, are generally semi-solid oil-in-water or water-in-oil emulsions. Creams can also be formulated using polymers such as polyethylene glycol. Creams are water-washable and do not leave the greasy residue that is sometimes present after the use of an ointment. They are able to absorb fluid from the skin and bring dissolved medication into good contact with the skin.

Gels are semi-solid systems consisting of suspensions made up of small inorganic particles or of large organic molecules interpenetrated by a liquid. Gels may be aqueous or alcohol based.

The composition can comprise varying amounts of the compound which inhibits the release of mediators from mast cells. In a preferred embodiment the compound is cromolyn sodium or nedocromil sodium and the concentration of the compound is from about 1% to about 10%; in a more preferred embodiment the concentration is from about 2% to about 6%; and in a most preferred embodiment the concentration is about 4% by weight.

The composition can contain additional ingredients, including antiseptics, preservatives, detergents, buffers, anesthetics, oils, alcohols, and coloring agents.

C) Administration of Compositions According to the Invention

The physician can determine the frequency and duration of treatment, based upon the characteristics of the individual patient and the severity of the symptoms.

In a preferred embodiment, the composition is applied from one to three times per day if applied to the vestibule, and from once or twice per day if applied to the vagina and the vestibule. For a given patient, the composition may be applied more or less frequently as determined by the physician.

In a preferred embodiment, the composition is applied for at least about three months. For a given patient, the composition may be applied for a longer or shorter duration as determined by the physician. Treatment may be continued as long as symptoms persist, and this may include long-term treatment in some patients.

The methods of the present invention are particularly useful where the underlying cause of the vulvar vestibulitis is unknown, in cases that have failed to respond to treatment of suspected causes, and in cases where one or more other therapeutic modalities have failed. Because the method of treatment is simple, inexpensive, and well tolerated, it can also be used as a first-line therapy.

EXAMPLES

The following examples illustrate the invention. These examples are illustrative only, and do not limit the scope of the invention.

Example 1

Treatment of Recalcitrant Vulvar Vestibulitis

A) Patients

Eleven patients were treated for recalcitrant vulvar vestibulitis. The median age was 31 years (range 23–46). Eight patients (73%) were nulliparous. Five patients (45%) had pre-existing vulvovaginal candidiasis with persistence of symptoms despite effective and continuous maintenance antifungal treatment. Nine patients (82%) had failed therapy with topical 0.1% triamcinolone ointment; ten (91%) did not improve or were intolerant of oral amitriptyline. The median duration of symptoms was 2.5 years (range 0.7–6).

Vulvar vestibulitis was diagnosed using Friedrich's criteria. (Friedrich, *J Reprod. Med.* 32:110–14, 1987). Symptoms were rated on a severity scale of 0 to 3, where 0=none, 1=mild, 2=moderate, and 3=severe. before treatment, the mean symptom severity score was 2.2±1 for irritation, 1.5±1.1 for burning, 1.0±0.8 for itching, and 2.8±0.5 for dyspareunia.

B) Preparation of a Cromolyn Sodium Cream

A 4% cromolyn sodium cream was prepared by dissolving powdered cromolyn sodium into a hydrophilic cream base (ACID MANTLE® CREME, manufactured by Sandoz Pharmaceuticals Corp., containing water, cetostearyl alcohol, white petrolatum, glycerin, synthetic beeswax, light mineral oil, sodium lauryl sulfate, aluminum sulfate, calcium acetate, methylparaben and white potato dextrin).

C) Treatment of Patients

The cromolyn sodium cream was applied topically, to the vulvar vestibule, twice daily for three months.

D) Results

The treatment was well tolerated by all patients. No adverse events were noted. After treatment ten patients had no symptoms with daily activity. Dyspareunia decreased to a score of 1.0±1.0 in the seven patients who were sexually active. Overall, nine patients felt markedly better, one slightly improved, and one unchanged.

Tables 1 and 2 show the pretreatment and postreatment symptom severity scores respectively. Following discontinuation of treatment four of the ten improved patients had a return of their symptoms.

TABLE 1

PRETREATMENT EVALUATION

| Symptom | Symptom Severity Score (N = 11) | | | |
|---|---|---|---|---|
| | 0 | 1 | 2 | 3 |
| Irritation | 1 | 1 | 4 | 5 |
| Burning | 3 | 1 | 5 | 2 |
| Itching | 3 | 5 | 3 | 0 |
| Dyspareunia (N = 7) | 0 | 0 | 1 | 6 |

TABLE 2

POSTREATMENT EVALUATION

| Symptom | Symptom Severity Score (N = 11) | | | |
|---|---|---|---|---|
| | 0 | 1 | 2 | 3 |
| Irritation | 10 | 1 | 0 | 0 |
| Burning | 10 | 1 | 0 | 0 |
| Itching | 11 | 0 | 0 | 0 |
| Dyspareunia (N = 7) | 2 | 4 | 0 | 1 |

Example 2

Randomized Placebo-Controlled Study

The first prospective double-blind, placebo-controlled study of a therapy for vulvar vestibulitis is designed to test the efficiency of cromolyn sodium in the treatment of vulvar vestibulitis, and also to test whether symptoms recur after discontinuation of therapy.

A) Project Protocol

Twenty patients are enrolled at each of two study centers, based on the following criteria:

Inclusion Criteria

1. Women age 18–50 years
2. Clinical diagnosis of vulvar vestibulitis, as described at pages 1–2, above
3. Symptom duration of greater than 6 months, less than 10 years
4. No other causes for vestibular erythema or tenderness based on history or clinical examination
5. Vaginal pH<4.5
6. Normal wet mount and KOH smear
7. Negative fungal culture
8. Only outpatients are eligible to enter the study
9. Written informed consent Exclusion Criteria 1. Other apparent cause for vaginitis or vulvar skin disorder
2. Patients with diabetes mellitus
3. Patients with HIV seropositivity
4. Pregnant or lactating women
5. Patients in other investigational studies
6. Patients with known allergy or hypersensitivity to cromolyn
7. Patients receiving topical or oral antibiotic therapy
8. Patients unwilling to give informed consent
9. Patients who have previously been enrolled in this study
10. Concurrent treatment for vulvar vestibulitis The pretreatment evaluation includes a baseline scoring of signs (erythema, extent of erythema, tenderness), symptoms (burning, irritation), and dyspareunia (in the sexually active patient subgroup), using the following scales:

Burning (non=0, mild=1, moderate=2, severe=3)

Irritation (0–3 scale)

Dyspareunia (0–3 scale)

Erythema (0–3 scale)

Tenderness (0–3 scale)

Extent of erythema (0=none, 1=posterior vestibule≦⅓ of entire vestibule, 2=⅓–⅔ of vestibule, 3=entire vestibule).

Patients are randomized to one of two arms, cromolyn sodium 4% cream or placebo cream. Randomization is 1:1 cromolyn sodium: placebo via a computer-generated randomization table. Enough of the cream to cover the tip of the index finger (~0.5 gm) is applied to the vulvar vestibule for three months. After treatment, patients are followed for an additional six weeks.

During both treatment visits (at about weeks 2, 4, 8 and 12) and follow-up visits, patients are asked whether their symptoms are subjectively reduced on a 0–100% of normal scale, where 0% represents how they felt at initiation of study. They are asked to rate both the amount of pain and the duration of time with pain. Signs and symptoms are scored as above. Severity scores are compared for the two groups (cromolyn sodium and placebo) using appropriate statistical tests.

B) Results

An interim analysis of the placebo-controlled study was performed. Sixteen of twenty enrolled patients were evaluable; nine received cromolyn sodium ("cromolyn").

The cromolyn and placebo groups were similar in terms of age (median 26 years), duration of symptoms (median 2.75 years), nulliparity (81%), coexistence of recurrent candidiasis requiring maintenance fluconazole (56%) to maintain negative fungal cultures, prior vestibulitis treatments, and severity of illness. At entry, the median scores were 3 out of 6 for symptoms, 5.5 out of 9 for signs, and 9 out of 15 total score.

Treatment with cromolyn changed symptoms by a median of 0 (range −4 to +2), signs by −4 (range −6 to +3), and the overall score by −4 (range −8 to +4). The placebo group had changes of 0 (range −4 to +4; p=0.70), −2 (range −4 to 0; p=0.09), and −2 (range −6 to +2; p=0.70) in the symptoms, signs, and overall scores respectively. Twelve patients were sexually active, with median scores of 3 for dyspareunia and 12 out of 18 for total symptoms/signs. In this subgroup, the median total score change was −5.5 (range −10 to +4) with cromolyn vs. −1.5 (range −6 to +2) with placebo (p=0.47).

Although both placebo and treatment groups improved, the patients that received cromolyn sodium improved more than patients that received placebo. This trend suggests that cromolyn sodium provides a clinical benefit in the treatment of vulvar vestibulitis.

Inflammation and tenderness are often intense at the hymenal junction. Some patients are reluctant to touch themselves to rub a medication on the tissue or unable to routinely apply it to the correct area. A vaginal application, for some patients, in addition to direct vestibular application may enable more medication to be in contact with the hymenal area. Normal vaginal discharge which comes into contact with the vestibule will bathe the vestibule with additional medication. We therefore expect that analogous results will be obtained when patients are treated by application to the vagina and the vestibule, as when the patients were treated by application to the vestibule alone as described in Examples 1 and 2 above.

All references discussed herein are incorporated by reference.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

We claim:

1. A method of treating vulvar vestibulitis in a patient comprising applying to the vestibule or the vestibule and the vagina of a patient an effective amount of a composition comprising a compound which inhibits the release of mediators from mast cells.

2. The method of claim 1 wherein the composition comprises cromolyn or a salt thereof.

3. The method of claim 2 wherein the composition comprises cromolyn sodium.

4. The method of claim 3 wherein the composition comprises from about 1% to about 10% by weight of cromolyn sodium.

5. The method of claim 3 wherein the composition comprises from about 2% to about 6% by weight of cromolyn sodium.

6. The method of claim 3 wherein the composition comprises about 4% by weight of cromolyn sodium.

7. The method of claim 1 wherein the composition comprises nedocromil or a salt thereof.

8. The method of claim 7 wherein the composition comprises nedocromil sodium.

9. The method of claim 8 wherein the composition comprises from about 1% to about 10% by weight of nedocromil sodium.

10. The method of claim 8 wherein the composition comprises from about 2% to about 6% by weight of nedocromil sodium.

11. The method of claim 8 wherein the composition comprises about 4% by weight of nedocromil sodium.

12. The method of claim 1 wherein the composition has a base selected from the group consisting of: creams, ointments and gels.

13. The method of claim 12 wherein the composition has a cream base.

14. The method of claim 12 wherein the composition has an ointment base.

15. The method of claim 1 wherein the composition further comprises one or more ingredients selected from the group consisting of: antiseptics, preservatives, detergents, buffers, anesthetics, oils, alcohols, and coloring agents.

16. The method of claim 1 wherein the composition is applied to the vestibule from about one to about three times per day.

17. The method of claim 1 wherein the composition is applied to the vestibule and the vagina from about one to about two times per day.

* * * * *

UNITED STATES PATENT AND TRADEMARK OFFICE
CERTIFICATE OF CORRECTION

PATENT NO.: 6,150,400

DATED : November 21, 2000

INVENTOR(S): Paul Nyirjesy and Steven P. Gelone

It is hereby certified that error appear(s) in the above-identified patent and that said Letters Patent are hereby corrected as shown below:

On the Title Page, next to [73] Assignee:, please delete "Presutti Laboratories, Arlington Heights, Ill." and insert next to [73] Assignee: --Temple University, Broad & Montgomery Avenue, Philadelphia, Pennsylvania 19122--

Signed and Sealed this

Fifteenth Day of May, 2001

*Attest:*

NICHOLAS P. GODICI

*Attesting Officer*       Acting Director of the United States Patent and Trademark Office